United States Patent
Ankorina-Stark et al.

(10) Patent No.: US 10,772,991 B2
(45) Date of Patent: Sep. 15, 2020

(54) POLYACRYLAMIDE HYDROGEL FOR USE IN THE PREVENTION AND/OR TREATMENT OF SYNOVITIS IN A MAMMAL

(71) Applicant: Contura International A/S, Søborg (DK)

(72) Inventors: Ieva Ankorina-Stark, Nivå (DK); Lise Hanne Christensen, Frederiksberg (DK)

(73) Assignee: Contura International A/S, Søborg (DK)

( * ) Notice: Subject to any disclaimer, the term of this patent is extended or adjusted under 35 U.S.C. 154(b) by 0 days.

(21) Appl. No.: 16/088,967

(22) PCT Filed: Mar. 30, 2017

(86) PCT No.: PCT/DK2017/050099
§ 371 (c)(1),
(2) Date: Sep. 27, 2018

(87) PCT Pub. No.: WO2017/167348
PCT Pub. Date: Oct. 5, 2017

(65) Prior Publication Data
US 2019/0307925 A1   Oct. 10, 2019

(30) Foreign Application Priority Data

Mar. 31, 2016   (EP) .................................. 16163450

(51) Int. Cl.
| | |
|---|---|
| *A61L 27/52* | (2006.01) |
| *A61P 19/02* | (2006.01) |
| *A61K 31/785* | (2006.01) |
| *A61L 27/16* | (2006.01) |
| *C08L 33/26* | (2006.01) |
| *A61K 31/16* | (2006.01) |
| *C08F 220/56* | (2006.01) |

(52) U.S. Cl.
CPC .............. *A61L 27/52* (2013.01); *A61K 31/16* (2013.01); *A61K 31/785* (2013.01); *A61L 27/16* (2013.01); *A61P 19/02* (2018.01); *C08F 220/56* (2013.01); *C08L 33/26* (2013.01); *A61L 2400/06* (2013.01); *A61L 2430/24* (2013.01)

(58) Field of Classification Search
CPC ......... A61L 27/52; C08F 220/56; A61P 19/02
See application file for complete search history.

(56) References Cited

FOREIGN PATENT DOCUMENTS

| | | |
|---|---|---|
| EP | 2 497 468 A1 | 9/2012 |
| WO | WO 02/16453 A1 | 2/2002 |
| WO | WO 2012/123385 A1 | 9/2012 |

OTHER PUBLICATIONS

Claire et al., "The role of synovitis in osteoarthritis", Ther Adv Musculoskeletal Dis, 2010, 2(6) 349-359.*
Shiel Jr., William C. "Osteoarthritis (OA or Degenerative Arthritis)" https://www.medicinenet.com/osteoarthritis/article.htm#osteoarthritis_facts.
International Search Report for PCT/DK2017/050099 dated May 29, 2017.

* cited by examiner

*Primary Examiner* — Gina C Justice
(74) *Attorney, Agent, or Firm* — Knobbe Martens Olson & Bear LLP

(57) ABSTRACT

The present invention relates to a polyacrylamide hydrogel for use in prevention and/or treatment of synovitis or pain associated with synovitis in a mammal by formation of an extra layer to the synovial membrane i.e. a sub-synovial layer and a novel synovial lining layer. Synovitis may occur in association with arthritis, such as osteoarthritis or rheumatoid arthritis, lupus, or gout, and the mammal suffering from synovitis is a preferably a human, a racing animal or a companion animal.

26 Claims, 2 Drawing Sheets

POLYACRYLAMIDE HYDROGEL FOR USE IN THE PREVENTION AND/OR TREATMENT OF SYNOVITIS IN A MAMMAL

CROSS REFERENCE TO RELATED APPLICATIONS

This application is a U.S. National Phase Application of PCT International Application Number PCT/DK2017/050099, filed on Mar. 30, 2017, designating the United States of America and published in the English language, which is an International Application of and claims the benefit of priority to European Patent Application No. 16163450.6, filed on Mar. 31, 2016. The disclosures of the above-referenced applications are hereby expressly incorporated by reference in their entireties.

TECHNICAL FIELD OF THE INVENTION

The present invention relates to a polyacrylamide hydrogel for use in prevention and/or treatment of synovitis in a mammal.

BACKGROUND OF THE INVENTION

Synovitis is the medical term for inflammation of the synovial membrane. This membrane lines joints which possess cavities, known as synovial joints. The condition is usually painful, particularly when the joint is moved. The joint usually swells due to synovial fluid collection.

In principal, changes of the synovial membrane can be inflammatory or non-inflammatory. To the latter group belong some benign tumors, such as tenosynovial giant cell tumor, lipoma or synovial chondromatosis. Rare non-inflammatory changes are the group of storage diseases. Inflammatory synovial diseases can be differentiated into crystal-induced arthropathy, such as gout and pseudogout, granulomatous diseases, such as tuberculosis, sarcoidosis and foreign body reactions and into the large group of non-granulomatous synovitis. This last group is by far the most common and often causes difficulties in assigning the histopathological findings to a definite diagnosis.

Hence, synovitis may occur in association with arthritis as well as lupus, gout, and other conditions. Synovitis is more pronounced in rheumatoid arthritis than in other forms of arthritis, and can thus serve as a distinguishing factor, although it is also present in many joints affected with osteoarthritis (OA).

Visco-supplementation is the process of injecting a gel-like substance into the joint. The substance is thought of as an additive to the joint fluid, thus lubricating the cartilage, and improving joint flexibility. This method of treatment, however, requires ongoing injections, as benefits are only temporary, because the currently used substances are degradable within weeks to months. Substances used in visco-supplementation include hyaluronic acid, or HA (Legend®, Hylartin® and Synacid®, Synvisc, Euflexxa, Supartz etc) and polysulfated glycosaminoglycans (PSGAGS) such as Adequan®.

Polyacrylamide hydrogel (PAAG) is known for its ability to support cellular growth in vitro and allow in-growth of host tissue cells in vivo. This has been documented in the soft subcutaneous tissues of mice, rats, rabbits, pigs and humans. The tissue integration begins immediately after PAAG injection as a sort of foreign body reaction to the PAAG. Host macrophages and foreign-body giant cells initially surround the PAAG and then invade it. In the process these cells are gradually transformed into fibroblasts and endothelial cells, which eventually form a thin vessel-bearing fibrous network inside the PAAG. However, the integration of PAAG in these tissues was not associated with any luminal surfaces and the PAAG contained macrophages and giant cells up until 14 months post injection.

WO 02/16453 discloses the use of a polyacrylamide hydrogel (PAAG) for treating e.g. arthritis. where the treatment is considered to be based on a lubricating and cushioning effect of the hydrogel. WO 2012/123385 discloses use of PAAG in the treatment and/or prevention of joint swelling and/or bone oedema in a mammal suffering from arthritis. Neither WO 02/16453 nor WO 2012/123385 discloses prevention and/or treatment of synovitis in a mammal.

Christensen and Daugaard (J Arthritis 5: 217; Sep. 16, 2016) provide a case report on the histological appearance of the synovial membrane after treatment of knee osteoarthritis with polyacrylamide gel injections.

The common symptoms for all types of synotivis in mammals include varied levels of pain in mammals. Synovitis symptoms can be treated with anti-inflammatory drugs such as NSAIDs. Another possibility is injection of steroids directly into the affected joint. Specific treatment depends on the underlying cause of the synovitis. Common to the various types of existing treatment is that they all have their disadvantages, e.g. short term treatment, toxicity and side-effects.

Hence, there is a need for an alternative or improved way to prevent and/or treat synovitis in a mammal. Also, there is a need for an alternative or improved way to prevent and/or treat synovitis pain in a mammal.

Surprisingly, the present inventors have found that polyacrylamide hydrogel (PAAG) is useful in the prevention and/or treatment of synovitis. Without being bound by a particular theory, the analgesic effect on synovitis is considered caused by a stable, long-lasting sub-synovial layer of PAAG traversed with thin strands of connective tissue and changes to synovial cell composition or cytokine production. Accordingly, the present invention surprisingly demonstrated the formation of a novel synovial lining layer after integration of the PAAG into mammal joints that persisted for at least 24 months.

SUMMARY OF THE INVENTION

Thus, an object of the present invention relates to prevention and/or treatment of synovitis in a mammal. Another object of the invention is the prevention and/or treatment of pain associated with synovitis.

In particular, it is an object of the present invention to provide an alternative or improved way to prevent and/or treat synovitis in a mammal that solves or reduces the above mentioned problems of the prior art with e.g. short term treatment, toxicity and side-effects.

Thus, one aspect of the invention relates to a polyacrylamide hydrogel for use in prevention and/or treatment of synovitis in a mammal by formation of a novel synovial lining layer.

Another aspect of the invention relates to a polyacrylamide hydrogel for use in prevention and/or treatment of synovitis in a mammal by formation of a sub-synovial layer.

In one embodiment, the invention relates to a polyacrylamide hydrogel for use in prevention and/or treatment of synovitis in a mammal by formation of a sub-synovial layer and a novel synovial lining layer.

In one embodiment, the invention relates to a method for the prevention and/or treatment of synovitis in a mammal, the method comprising administering to said 35 mammal a polyacrylamide hydrogel to form a novel synovial lining layer.

In one embodiment, the invention relates to a method for the prevention and/or treatment of synovitis in a mammal, the method comprising administering to said mammal a polyacrylamide hydrogel to form a sub-synovial layer.

In one embodiment, the invention relates to a method for the prevention and/or treatment of synovitis in a mammal, the method comprising administering to said mammal a polyacrylamide hydrogel to form a sub-synovial layer and a novel synovial lining layer.

In another embodiment, the invention relates to use of a polyacrylamide hydrogel for preparation of a medicament for prevention and/or treatment of synovitis in a mammal by formation of a novel synovial lining layer.

In another embodiment, the invention relates to use of a polyacrylamide hydrogel for preparation of a medicament for prevention and/or treatment of synovitis in a mammal by formation of a sub-synovial layer.

In another embodiment, the invention relates to use of a polyacrylamide hydrogel for preparation of a medicament for prevention and/or treatment of synovitis in a mammal by formation of sub-synovial layer and a novel synovial lining layer.

A further aspect of the invention relates to a polyacrylamide hydrogel for use in prevention and/or treatment of synovitis pain in a mammal by formation of a novel synovial lining layer.

A further aspect of the invention relates to a polyacrylamide hydrogel for use in prevention and/or treatment of synovitis pain in a mammal by formation of a sub-synovial layer.

A further embodiment of the invention relates to a polyacrylamide hydrogel for use in prevention and/or treatment of synovitis pain in a mammal by formation of a sub-synovial layer and a novel synovial lining layer.

One embodiment of this aspect of the invention relates to a method for the prevention and/or treatment of synovitis pain in a mammal, the method comprising administering to said mammal a polyacrylamide hydrogel to form a novel synovial lining layer.

One embodiment of this aspect of the invention relates to a method for the prevention and/or treatment of synovitis pain in a mammal, the method comprising administering to said mammal a polyacrylamide hydrogel to form a sub-synovial layer.

One embodiment of this aspect of the invention relates to a method for the prevention and/or treatment of synovitis pain in a mammal, the method comprising administering to said mammal a polyacrylamide hydrogel to form a sub-synovial layer and a novel synovial lining layer.

Another embodiment relates to use of a polyacrylamide hydrogel for preparation of a medicament for prevention and/or treatment of synovitis pain in a mammal by formation of a novel synovial lining layer.

Another embodiment relates to use of a polyacrylamide hydrogel for preparation of a medicament for prevention and/or treatment of synovitis pain in a mammal by formation of a sub-synovial layer.

Another embodiment relates to use of a polyacrylamide hydrogel for preparation of a medicament for prevention and/or treatment of synovitis pain in a mammal by formation of a sub-synovial layer and a novel synovial lining layer.

DETAILED DESCRIPTION OF THE INVENTION

Figure 1:
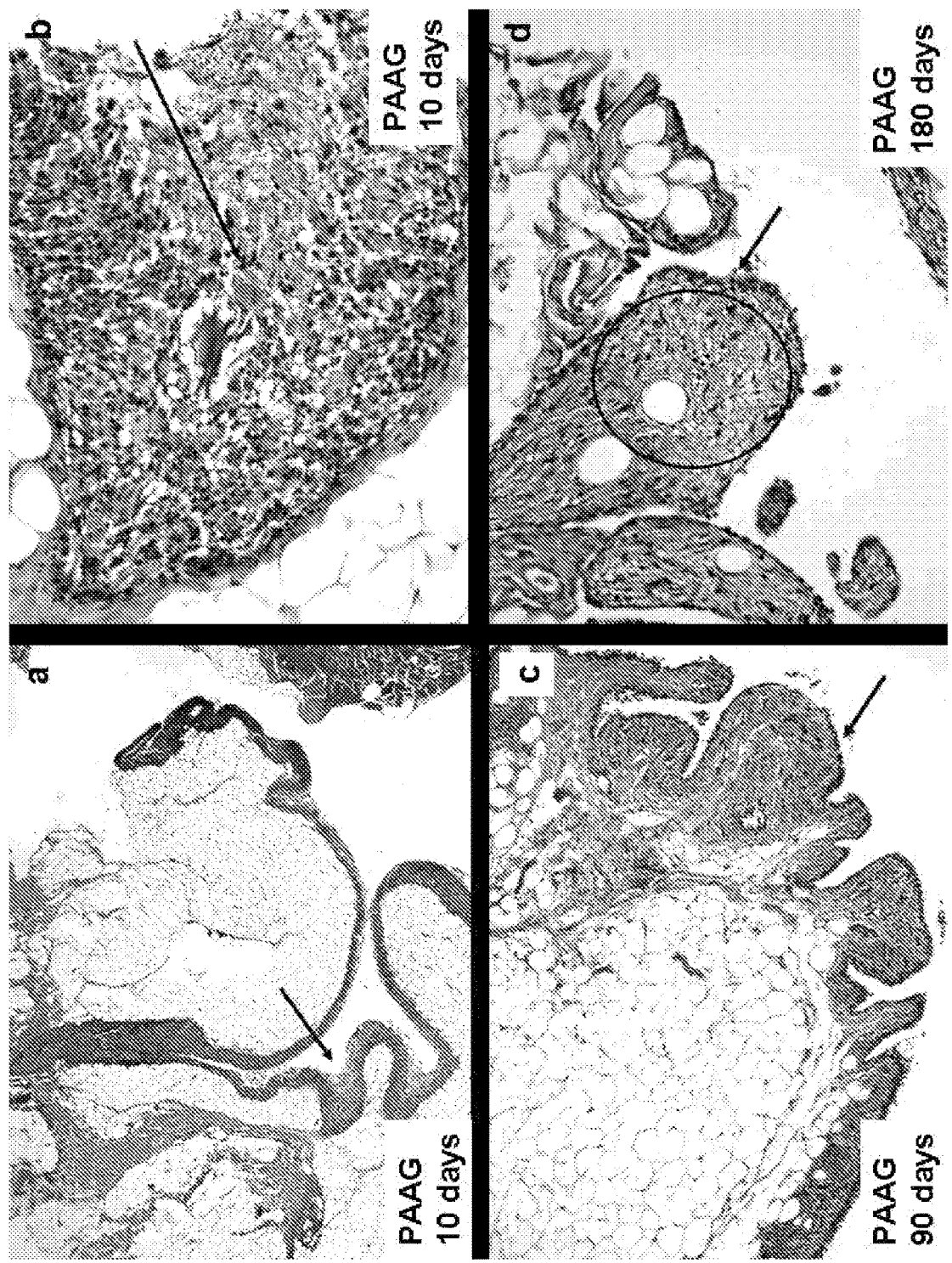
FIG. 1 shows a rabbit normal knee joint injected with PAAG after 10 days (a, b), after 90 days (c) and after 180 days (d). At 10 days the PAAG was still present in the cavity just below the synovial lining (a, arrow) and was dominated by 30 proliferating synovial cells (b, arrow). At 90 and 180 days the synovial lining was intact (c, d, arrows), and the integrated PAAG contained only scattered chronic inflammatory cells intermixed with the fibrous network (d, circled). HE×60 (a), HE×400 (b), HE×100 (c), HE×300 (d).

PAAG is prepared as described in WO 02/16453, and further in WO 2012/123385, which are hereby incorporated by reference. The PAAG may comprise any embodiment of the hydrogel as described in WO 02/16453 and WO 2012/123385.

As noted above, one aspect of the present invention relates to a polyacrylamide hydrogel for use in prevention and/or treatment of synovitis in a mammal by formation of a sub-synovial layer and/or formation of a novel synovial lining layer. In a related aspect, the invention relates to a polyacrylamide hydrogel for use in prevention and/or treatment of synovitis pain in a mammal by formation of a sub-synovial layer and/or formation of a novel synovial lining layer.

In an embodiment, the sub-synovial layer and/or the novel synovial lining layer is present/persists for up to 1 month (M) or more, such as 2 M, such as 3 M, such as 4 M, such as 5 M, such as 6 M, such as 7 M, such as 8 M, such as 9 M, such as 10 M, such as 11 M, such as 12 M, such as 13 M, such as 14 M, such as 15 M, such as 16 M, such as 17 M, such as 18 M, such as 19 M, such as 20 M, such as 21, such as 22 M, such as 23 M, such as 24 M, such as 24 M, such as 25 M, such as 26 M, such as 27 M, such as 28 M, such as 29 M, such as 30 M, such as 30-35 M, such as 35-40 M, such as 40-45 M, such as 45-50 M, such as 50-55 M, such as 55-60 M or more than 60 M.

According to the invention, formation of a sub-synovial layer and formation of a novel synovial lining layer means that in the joints, upon injection of a polyacrylamide hydrogel of the invention in the joint cavity, the body adds/forms a novel sub-synovial layer on top of the original synovial membrane. In other words, an extra layer is added to the synovial membrane. On top of the novel sub-synovial layer facing the joint cavity, a novel synovial lining layer is formed/added. Surprisingly, the added novel sub-synovial layer in the synovial membrane and the novel synovial lining layer are both stable, and persist for a very long time.

According to the invention, pain is assessed by use of The Western Ontario and McMaster Universities Arthritis Index (WOMAC). It is a proprietary set of standardized questionnaires used by health professionals to evaluate the condition of patients with osteoarthritis of the knee and hip, including pain, stiffness, and physical functioning of the joints. Hence, the WOMAC is used to assess pain in the knee, hip, elbow, the metacarpal-phalangeal and interphalangeal joints in hands and feet, the sesamoid joint and/or the temporomandibular joint in humans. Pain in mammals such as horses or dogs is assessed subjectively by a veterinarian.

Preferably, according to the invention, a polyacrylamide hydrogel is administered by injection under sterile conditions. In one embodiment, the polyacrylamide hydrogel is administered by intraarticular injection.

The injection of the PAAG may be performed under local anaesthesia, but local anaesthesia is not necessarily required. However, the procedure is preferably performed under sterile conditions. Any hair covering the injection area is cropped and the skin thoroughly rinsed e.g. with chlorhexidine and ethanol (e.g. 3 times interchangeably). Then, the cannula is inserted into the joint cavity and it is checked by aspiration that it is placed properly intraarticularly. Generally, the joint is emptied for at least the amount of liquid which it has been decided to inject and the desired amount of the PAAG is then injected. An antibiotic may be included in the PAAG in order to prevent iatrogenic infection of the joint.

In one embodiment of the invention, 0.1-20 ml polyacrylamide hydrogel is administered by injection into the intraarticular cavity.

In another embodiment, 0.1-20 ml polyacrylamide hydrogel is administered by injection into the intraarticular cavity at least once, such as twice, such as three times, such as four times, such as 5 times, such as 6 times, such as 7 times, such as 8 times, such as 9 times, such as 10 times into the intraarticular cavity. In a further embodiment 0.1-20 ml polyacrylamide hydrogel is administered at least 1-2 times in total, such as 1-5 times in total, such as 1-10 times in total, such as 1-15 times in total, such as 1-20 times in total, such as 1-30 times in total, such as 1-40 times in total, such as even more than 40 times in total. The administration can be performed during a period of several years, such as during a period of 1 year, 2, 3, 4, 5, 6, 7, 8, 9 or 10 years.

In still another embodiment, 0.1-20 ml polyacrylamide hydrogel is administered by injection into the intraarticular cavity at regular intervals, for example once every 2 weeks, such as every 4 weeks, such as every 6 weeks, such as every 8 weeks, such as every 10 weeks, such as every 12 weeks, such as every 14 weeks, such as every 16 weeks or even longer into the intraarticular cavity.

In yet another embodiment, 0.1-20 ml polyacrylamide hydrogel is administered by injection into the intraarticular cavity at intervals of e.g. once every 2 weeks, such as every 4 weeks, such as every 6 weeks, such as every 8 weeks, such as every 10 weeks, such as every 12 weeks, such as every 14 weeks, such as every 16 weeks or such as even longer for a total of e.g. 2 injections, such as 3, such as 4, such as 5, such as 6, such as 7, such as 8, such as 9, such as 10 injections in total.

0.1-20 ml polyacrylamide hydrogel may also be administered by injection into the intraarticular cavity once a year or more, such as twice, 3 times, 4, 5, 6, 7, 8, 9, 10, 11 or 12 times every year for one year or more, e.g. 2, or 3, or 4, or 5, or 6, or 7, or 8, or 9 or 10 years.

An appropriate amount of polyacrylamide hydrogel will be in the range of 0.1 ml to 20 ml, such as 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18 or 19 ml. However, it is not advisable to inject so much hydrogel that the joint is expanded. The exact amount will be decided by the treating physician or veterinarian on the basis of the size of the joint and the severity of the synovitis.

Preferably, an amount of 1-2 ml or more, such as 1-3, such as 1-4, such as 1-5, such as 1-6, such as 1-7, such as 1-8, such as 1-9, such as 1-10, such as 1-11, such as 1-12, such as 1-13, such as 1-14, such as 1-15, such as 1-16, such as 1-17, such as 1-18, such as 1-19 ml is administered.

In an embodiment of the invention, the mammal is a human, a racing animal or a companion animal. The most relevant mammals are humans, racing animals such as horses and camels, and companion animals such as cats and dogs but also other 35 mammals in need of treatment such as elephants, giraffes, tigers etc. In one preferred embodiment, the mammal is a human, a horse or a dog. In an even more preferred embodiment, the mammal is a human.

Any joint affected by synovitis may be treated. Non-limiting examples are knee, hip, elbow, the metacarpal-phalangeal and interphalangeal joints in hands and feet of humans, fetlock, coffin, pastern, stiffel, and knee joint of the hind legs of horses, and elbow, knee and hip of cats and dogs. Also treatment of other joints such as the sesamoid and the temperomandibular joints may be relevant.

In another preferred embodiment of the invention, the mammal to be treated is a human and the joint or joints which is/are to be treated is the knee, hip, elbow, the metacarpal-phalangeal and interphalangeal joints in hands and feet, the sesamoid joint and/or the temperomandibular joint.

In yet another embodiment of the invention, the mammal to be treated is a horse and the joint or joints which is/are to be treated is the fetlock, coffin, pastern, stifle, and/or knee joint of the hind legs.

In a still further embodiment of the invention the mammal to be treated is a dog and the joint or joints which is/are to be treated is the elbow of the front leg or the knee or hip joint of the hind legs.

In yet a further embodiment of the invention the mammal is suffering from synovitis.

In an embodiment of the invention the mammal is suffering from arthritis, such as osteoarthritis or rheumatoid arthritis, lupus, or gout.

Arthritis is a group of conditions involving damage to the joints of the body. There are over 100 different forms of arthritis. The most common form, osteoarthritis (degenerative joint disease) is a result of trauma to the joint, infection of the joint, or age. Other arthritis forms are rheumatoid arthritis, psoriatic arthritis, and related autoimmune diseases. Septic arthritis is caused by joint infection.

Osteoarthritis (OA) is a painful, debilitating joint disease with no known cure. It is characterized by heat, pain, swelling, crepitus (a crackling, crinkly, or grating feeling or sound under the skin), and a decreased range of motion in affected joints. In humans it affects the hands, knees, hips, spine and other joints. Horses suffer from joint osteoarthritis in primarily coffin, pastern, fetlock, carpal and stiffle joints, and the incidence is dependent on age, weight and breed.

Rheumatoid arthritis (RA) is a long-lasting autoimmune disorder that primarily affects joints.

Lupus or lupus erythematosus is a name given to a collection of autoimmune diseases in which the human immune system becomes hyperactive and attacks normal, healthy tissues, such as joints.

Gout (also known as podagra when it involves the joint at the base of the big toe) is usually characterized by recurrent attacks of inflammatory arthritis—a red, tender, hot, and swollen joint.

Regardless of the type of arthritis, the common symptoms for all arthritis disorders include varied levels of pain, swelling, joint stiffness and sometimes a constant ache around the joint(s). The major complaint by individuals who have arthritis is joint pain. Pain is often constant and may be localized to the joint affected. The pain from arthritis occurs due to inflammation that occurs around the joint, damage to the joint from disease, daily wear and tear of joint, muscle strains caused by forceful movements against stiff, painful joints and fatigue.

In another embodiment of the invention the mammal is suffering from osteoarthritis or rheumatoid arthritis.

In a further embodiment of the invention the mammal is suffering from osteoarthritis.

In yet a further embodiment of the invention the mammal is suffering from rheumatoid arthritis.

Preparation of the Polyacrylamide Hydrogel (PAAG)

The hydrogel may be prepared as described in WO 02/16453, hereby incorporated by reference. In the following, the polyacrylamide hydrogel may be abbreviated PAAG.

The hydrogel may comprise any embodiment of the hydrogel as described in WO 02/16453 and WO 2012/123385. Preferably, the hydrogel comprises 0.5 to 25% by weight polyacrylamide, based on the total weight of the hydrogel. The hydrogel typically further comprises at least 75% by weight pyrogen-free water or saline solution, preferably pyrogen-free water.

The hydrogel is obtainable by combining acrylamide and cross-linking monomers, initiating polymerisation by radical initiation; and washing with pyrogen-free water or saline solution, the combining being in amounts and the washing being such as to give about 0.5 to 25% by weight polyacrylamide, based on the total weight of the hydrogel. The hydrogel thus obtained is both biostable and biocompatible, and is not resorbed by the body.

Typically, the hydrogel is obtained by combining acrylamide and cross-linking agent, such as N,N'-methylene bis-acrylamide, in a molar ratio of 150:1 to 1000:1. The cross-linking agent, such as N,N'-methylene bis-acrylamide, serves to provide cross-linking between polymer chains and the molar ratio may be varied to provide various cross-linking densities of the hydrogel. The conditions for obtaining the hydrogel may be modified according to, for instance, the nature of the joint into which the hydrogel is intended to be injected. The desired rheological properties, such as elasticity, may be controlled at least in part by the solid weight content of the hydrogel. The hydrogel of the invention comprises about 0.5 to 25% by weight polyacrylamide, based on the total weight of the hydrogel. In suitable embodiments of the invention, the hydrogel comprises less than 15% by weight polyacrylamide, based on the total weight of the hydrogel, preferably less than 10% by weight, more preferably less than 7.5% by weight, even more preferably less than 5%, most preferably less than 3.5% by weight polyacrylamide, based on the total weight of the hydrogel.

The combining involves combining of the component reagents acrylamide and cross-linking agent, such as N,N'-methylene bis-acrylamide, typically degassed and typically in a manner to minimise operator contact. The reagent components may optionally be combined previously to form an inert mixture. An inert mixture is one wherein no chemical reaction proceeds among the component reagents. The combining involves combining acrylamide, cross-linking agent, such as N,N'-methylene-bis-acrylamide, and a radical initiator component to initiate polymerisation. In a suitable embodiment, an inert premixture of acrylamide, cross-linking agent, such as N,N'-methylene-bis-acrylamide, and N,N,N',N'-tetramethylene-ethylene-diamine (TEMED) is combined with an ammonium persulfate (AMPS) initiator solution. However, the components may be combined as singularities or as alternative plural premixtures.

Acrylamide and cross-linking agent, such as N,N'-methylene-bis-acrylamide, are suitably combined in a molar ratio of about 150:1 to 1000:1, typically about 150:1 to 900:1, preferably about 175:1 to 800:1, more preferably about 200:1 to 600:1, most preferably from 250:1 to 600:1. As shown in Tables 2 and 3, hydrogels of differing solid-weight content and rheological properties may be controllably prepared. The hydrogel having the desired rheological characteristics has been obtained by combining acrylamide and N,N'-methylene-bis-acrylamide in a ratio of about 250:1, about 260:1, about 270:1, about 280:1, about 290:1, about 300:1, about 310:1, about 320:1, about 330:1, about 340:1, about 350:1, about 360:1, about 370:1, about 380:1, about 390:1, about 400:1, about 410:1, about 420:1, about 430:1, about 440:1, about 450:1, about 460:1, about 470:1, about 480:1, about 490:1 and about 500:1.

Particularly in the embodiment wherein the hydrogel is injected into a joint, the elasticity of the hydrogel is of great relevance. In a preferred embodiment, the hydrogel of the invention has an elasticity modulus of about 1 to 200 Pa, such as about 2 to 175 Pa, typically about 5 to 150 Pa, such as 10 to 100 Pa. Persons skilled in the art will be aware of how to obtain a hydrogel with a suitable elasticity for the intended use. See also the examples below, which describe preparation of hydrogels with low, medium and high elasticity.

The hydrogel comprises at least 75% by weight pyrogen-free water or saline solution, preferably pyrogen-free water. In a suitable embodiment of the invention, the hydrogel comprises at least 80% by weight pyrogen-free water or saline solution, preferably at least 85%, more preferably at least 90%, even more preferably at least 95% by weight pyrogen-free water or saline solution.

A suitable saline solution has an osmolarity similar to that of interstitial fluid. Suitable saline solutions include but are not limited to the group comprising 0.25-1% aqueous sodium chloride, a Ringer-Lockart solution, an Earle solution, a Hanks solution, an Eagle medium, a 0.25-1% glucose solution, a potassium chloride solution, and a calcium chloride solution. In a preferred embodiment, the saline solution is a 0.8-1% aqueous sodium chloride solution, such as a 0.8, 0.9 or 1% aqueous sodium chloride solution, most preferably about 0.9% aqueous sodium chloride.

As will be obvious to the person skilled in the art, in the embodiment wherein saline solution is used either for the preparation of the PAAG and/or for the washing of the PAAG, the solid-weight content of the PAAG will be higher than the contribution made by the polyacrylamide, but typically not more than an additional 1%.

In a particularly suitable embodiment of the invention, the hydrogel comprises about 2.5% by weight polyacrylamide, based on the total weight of the hydrogel and about 97.5% pyrogen-free water.

Pyrogen-free water or saline solution is used for washing the hydrogel in a washing process. The washing process serves, in part, to remove all but trace amounts of the monomers acrylamide and cross-linking agent, such as N,N'-methylene-bis-acrylamide. These monomers are toxic to the patient as well as detrimental to the stability of the hydrogel. The washing process is preferably such that the concentrations of the remaining monomers acrylamide and cross-linking agent, such as N,N'-methylene-bis-acrylamide, are below 50 ppm, more preferably below 40 ppm, such as below 30 ppm, most preferably below 20 ppm, typically below 10 ppm, particularly preferably below 5 ppm.

Cross-Linking Agents

The hydrogel according to the present invention may contain a cross-linking agent selected from the group consisting of N, N'-methylene-bis-acrylamide, N, N'-ethylene-bis-acrylamide, ethylene-bis (oxyethylene nitril)-tetracetic oxide, ethylene-bis-(oxyethylene nitril) tetracetic acid, and mixtures thereof. In one embodiment, said cross-linking agent is selected from the group consisting of N,N'-methylene-bis-acrylamide, N,N'-ethylene-bis-acrylamide, and mixtures thereof. In a further embodiment, said cross-linking agent is N,N'-methylene-bis-acrylamide.

It should be noted that embodiments and features described in the context of one of the aspects of the present invention also apply to the other aspects of the invention.

All references cited in the present application, are hereby incorporated by reference in their entirety.

The invention will now be described in further detail in the following non-limiting examples.

EXAMPLES

Example 1—Preparation of Hydrogel

Preparation of Hydrogel:

The PAAG is a polyacrylamide gel manufactured by a polymerisation of the monomers of acrylamide (AM) and N,N'-methylene-bis-acrylamide (bisAM). The finished product may have different elasticity modules.

The hydrogel typically contains approximately 95% water. The concentration of the monomers acrylamide and N,N'-methylene-bis-acrylamide has been shown to be less than 10 ppm and is adequate for the desired stability of the final product, often less than 5 ppm.

The finished product must conform with respect to pH, absence of heavy metals, refractive index, stability, absence of pyrogens, and must be sterile, practically inert, and be substantially free of monomers.

Preparation 1.1

The synthetic preparation suitably involves the following operations:

1. Two mixtures, A1 and A2, are prepared. A1 comprises water, acrylamide, N,N'-methylene-bis-acrylamide, N,N,N',N'-tetramethylene-ethylene-diamine (TEMED). A2 comprises water and ammonium persulfate;
2. The two mixtures are combined in the following ratio: 1990 mL of A1 and 10 mL of A2 and kept at 45° C. and degassed with nitrogen for 20 seconds;
3. The reaction mixture is cast into several 100 mL beakers;
4. Polymerisation is allowed to occur for 0.5 to 1.5 hours;
5. The gel is demolded;
6. Residual monomers are extracted and with equilibration in WFI water for 92 hours, changing the water several times, typically 8 times during the 92 hours;
7. The purified gels are homogenised by grinding with a vertically oscillating grid;
8. A syringe is filled with the homogenised gel material;
9. Autoclavation of the syringe A typical method for preparing the hydrogel may be summarised as:

Preparation 1.2

Process Summary

The gel is prepared by mixing an aqueous monomer solution of acrylamide (AM) and N,N'-methylene-bis-acrylamide (bisAM) as cross-linker with N,N,N',N'-tetramethylene ethylene diamine (TEMED) as co-initiator and ammonium persulfate (AMPS) as free-radical initiator (redox-system). By degassing a bulk solution with nitrogen, polymerisation starts. After final polymerisation the gel is transferred into a washing tank with net trays onto which the gel is placed. During water washing, the gel swells and monomer residues are extracted. The swollen gel is fed and evacuated in a filling unit having the gel delivered in a syringe, which is autoclaved. Two alternate formulations have been prepared, a lower- and a higher-end elasticity formulation.

TABLE 1

| Chemical constituent | lower end elasticity | higher end elasticity |
|---|---|---|
| acrylamide | 502 g | 547 g |
| N,N'-methylene-bis-acrylamide | 2.2 g | 4.6 g |
| TEMED | 3.0 g | 2.6 g |
| AMPS | 5.4 g | 5.0 g |
| Non-pyrogenic water | Add 10 litre | Add 10 litre |

The above are typical preparations of the hydrogel and may be adjusted within certain ranges.

Preparation 1.3

Polyacrylamide Formulations from Inline Cross-Linking Process

A particularly interesting method of preparing the hydrogels of the invention involves an inline cross-linking process. Two individual and eventually degassed flows, one being a pre-mix of acrylamide, N,N'-methylene-bis-acrylamide (the cross-linker) and TEMED, the other being the AMPS initiator solution, are pumped into a static mixer for mixing, chemical initiation and subsequent extrusion downstream into a pipe reactor made of Teflon or steel in which the polymerisation occurs. Washing of the gel is simplified due to high surface area of gel from reactor.

By selecting monomer, cross-linker and initiator concentrations and their relative molar ratios, and by regulating the two flow rates and the polymerisation temperatures, it is possible to produce gels that are varying in degree of crosslinking and in solids content.

Preparation 1.4

The reagents were combined in ratios described in Tables 2, 3 and 4, and washed as described in the Tables (with pyrogen-free water unless indicated otherwise) to give low, medium, and high elasticity formulations. Hydrogels with solid weight contents between 0.5 and 25% polyacrylamide were prepared.

TABLE 2

| Process parameters and features of resulting gel: low elasticity formulations | | | | | | | | |
|---|---|---|---|---|---|---|---|---|
| | Iv1 | Iv2 | Iv3 | Iv4 | Iv5 | Iv6 | Iv7[d] | Iv8[e] |
| washing time (hrs) | a) | 19.5 | 73.75 | 92 | 94.3 | 72.8 | 93.6 | 93.9 |

TABLE 2-continued

Process parameters and features of resulting gel: low elasticity formulations

| | | | | | | | | |
|---|---|---|---|---|---|---|---|---|
| dry matter[i] (%) | 2.55 | 2.08 2.36 | 2.63 2.58 2.09 | 2.87 2.67 | 2.89 2.82 | 3.15 2.90 | 3.68 3.57 | 3.17 3.52 |
| molar ratio AM:bisAM | b) | 976 | 700 | 488 | 366 | 3239 | 488 | 488 |
| molar ratio AM + bisAM:TEMED | 252 | 252 | 253 | 251 | 252 | 249 | 252 | 252 |
| molar ratio AM + bisAM:AMPS | 298 | 299 | 298 | 298 | 298 | 299 | 298 | 298 |
| residual monomer in ppm | c) | 89 | 5 | 2.97 | 2 | 5 | 1.4 | 0.97 |
| elasticity G' in Pa | 0.16 | 5.23 | 14.3 20.1 | 26.6 | 57.05 | 71.7 | 39.2 | 28.5 |
| gelation time (min) | liquid | highly viscous liquid | 12 | 2 | 2 | 2 | 2.5 | 2.5 |

| | Iv9 | Iv10 | Iv11 | Iv11 | Iv12 |
|---|---|---|---|---|---|
| washing time (hrs) | 121 | 96.4 | | | |
| dry matter (%) | 2.18 | (5.10)[f] | (10.2)[f] | (10.1)[f] | (20.2)[f] |
| molar ratio AM:bisAM | 701 | 701 | 488 | 488 | 488 |
| molar ratio AM + bisAM:TEMED | 252 | 252 | 252 | 504 | 2016 |
| molar ratio AM + bisAM:AMPS | 298 | 298 | 298 | 596 | 2385 |
| residual monomer in ppm | 0.97 | | | | |
| elasticity G' in Pa | 28.5 | 11.1 | (911)[g] | (1240)[g] | (9460)[g] |
| gelation time (min) | | 3.17 | 0.00 | 1.21 | 3.5[h] |

[a]material was liquid so washing was a dilution
[b]infinite
[c]since washing was not an extraction but a dilution, the residual monomer was merely decreased by the dilution factor (508 ppm to 254 ppm).
[d]casting and washing done using 0.9% NaCl aqueous solution
[e]casting with water; washing done using 0.9% NaCl aqueous solution
[f]pre-wash values - washing typically reduces value by 30-55%
[g]pre-wash values - washing typically reduces value by 20-40%
[h]highly notch sensitive
[i]variations in values may be due to measurement performance techniques or to location in the batch from which sample was taken

TABLE 3

Process parameters and features of resulting gel: medium elasticity formulations

| | mv1 | mv2 | mv3 | mv4 | mv5 |
|---|---|---|---|---|---|
| washing time (hrs) | 97 | 211.5 | 96 | 94.8 | 90.3 |
| dry matter (%) | 3.14 | 2.49 | 3.25 | 3.29 | 3.22 |
| molar ratio AM:bisAM | 310 | 310 | 290 | 289 | 289 |
| molar ratio AM + BISAM:TEMED | 252 | 252 | 252 | 251 | 252 |
| molar ratio AM + BISAM:APS | 299 | 299 | 299 | 299 | 299 |
| residual monomer in ppm | 1.6 | | 1.5 | | |
| elasticity G' in Pa | 108.5 | | 129 | 133.5 | |
| gelation time (min) | 2.5 | 2.5 | 2.18 | | |

TABLE 4

Process parameters and features of resulting gel: high elasticity formulations

| | hv1 | hv2 | hv3 | hv4 | hv5 |
|---|---|---|---|---|---|
| washing time (hrs) | 119.5 | 516 | 122 | 95.5 | 116.7 |
| dry matter (%) | 3.47 | 2.5 | 3.56 | 3.83 | 3.42 |
| molar ratio AM:bisAM | 260 | 260 | 260 | 260 | 260 |
| molar ratio AM + bisAM:TEMED | 315 | 315 | 604 | 313 | 314 |
| molar ratio AM + bisAM:AMPS | 376 | 376 | 755 | 375 | 376 |
| residual monomer in ppm | 0.2 | | | | |
| elasticity G' in Pa | 343 | 274 | | 314.5 | |
| gelation time (min) | 2.18 | 2.18 | 7.5 | | |

Example 2—Study of Integration of PAAG (Polyacrylamide Hydrogel) into Animal Joints The aim of this histopathological study was to investigate if, and if so where, intraarticular injection of PAAG is integrated in normal and OA animal joints, and if this integration is sustained over time.

Methods

Two animal joint types were examined. Firstly, we conducted a prospective, longitudinal, controlled study on normal knee joints in rabbits, and secondly, a post mortem examination was made on OA horse joints which had been treated with PAAG at different times prior to death. The PAAG used in all these cases was Aquamid Reconstruction@ (Contura International A/S, Soeborg, Denmark). Ethical approval was obtained from the Danish Animal Welfare Organization (dyreforsøgstilsynet, reference J.nr. 2010/561-1774).

Prospective Comparative Study in Normal Rabbit Joints

A total of 10 two-year old New Zealand white rabbits were used. The first 4 received injections in the right knee with 2.5% PAAG and in the left knee saline as control. The remaining 6 rabbits also received PAAG injections in the right knee but in the left knee they received hyaluronan (HA, Durolane 20 mg/ml, Galderma, Switzerland) as a control. The volume of injected PAAG, saline or HA was 0.3 ml per knee. This was administered after having removed a few drops of joint fluid. The rabbits were observed daily for well-being and their weight was measured once a week and they were kept under standard conditions in pairs. The first 4 rabbits (saline control group) were sacrificed after 10 days. The remaining 6 rabbits were sacrificed, 2 at a time, after 3, 6 and 12 months. For all 10 rabbits both knee joints were removed and inspected macroscopically. All synovial, cartilage, tendon and fatty tissue of the joint was removed and processed for histopathological examination using H&E and van Gieson/Alcian blue stains as tissue markers.

A Study of Osteoarthritic Joints in the Horse

This study included 7 horses (age 5-13 years, median 10 years) presenting a total of 13 joints with veterinarian-diagnosed OA that had been treated with PAAG. Five joints without OA served as controls. The horses were part of a large prospective clinical study carried out at 3 different equine centers, where 1-4 (mean 2) ml of PAAG had been injected per joint and where the effect of the treatment was followed postoperatively for up to 2 years. Histopathological examination was carried out on leg joints from horses having died during that period. Treatment with PAAG had been performed from 7 days to 2 years previously. All horses had been euthanized for causes unrelated to the PAAG treatment. After dissection and macroscopic inspection of the joints, all synovial tissue representing the inner capsule was routinely fixed, paraffin embedded and stained for light microscopy. Samples from the cartilage were also examined (2 from each joint).

Results—Rabbit Study

The rabbits with normal joints were all healthy at injection and remained so during the study with no change in joint movement (e.g. activity restriction or limping) at any time. On gross inspection there were no differences other than 2 cases of slight capsule hemorrhage at the injection site. Upon opening the joint cavity, both synovial fluid and the inner synovial lining appeared slightly thickened on the PAAG-treated side as compared to the saline-treated side at day 10. No macroscopic differences could be discerned between PAAG and HA treated joints at any time point.

Light microscopy on the PAAG treated side at day 10 showed a novel synovial lining layer which was 5-10-fold thicker than on the saline injected side (FIG. 1a), due to the PAAG containing proliferating synovial cells (FIG. 1b).

At days 90, 180 and 360 the synovial layer was still up to 10-times thickened on the PAAG treated side (FIG. 1c), and the synovial lining was present on top of the PAAG facing the cavity. By now only scattered synovial cells were seen inside the PAAG intermixed with a fine fibrous network (FIG. 1d, and no PAAG was found within the joint cavity (FIGS. 1c and 1d).

Results—Horse Study

Macroscopic findings: Coffin, fetlock and knee joints had been treated with PAAG. Three untreated coffin joints and 2 fetlock joints served as controls. Upon opening the joint cavity, various grades of osteophyte formation and/or cartilage defect(s) could only be seen in 3 of the 5 treated fetlock joints. The PAAG appeared as a thick, smooth, glistening, yellow substance or in the coffin joint as small clear deposits along the inner part of the anterior longitudinal tendon facing the cavity. Free PAAG inside the cavity could not be discerned from joint fluid on naked eye inspection.

Figure 2:
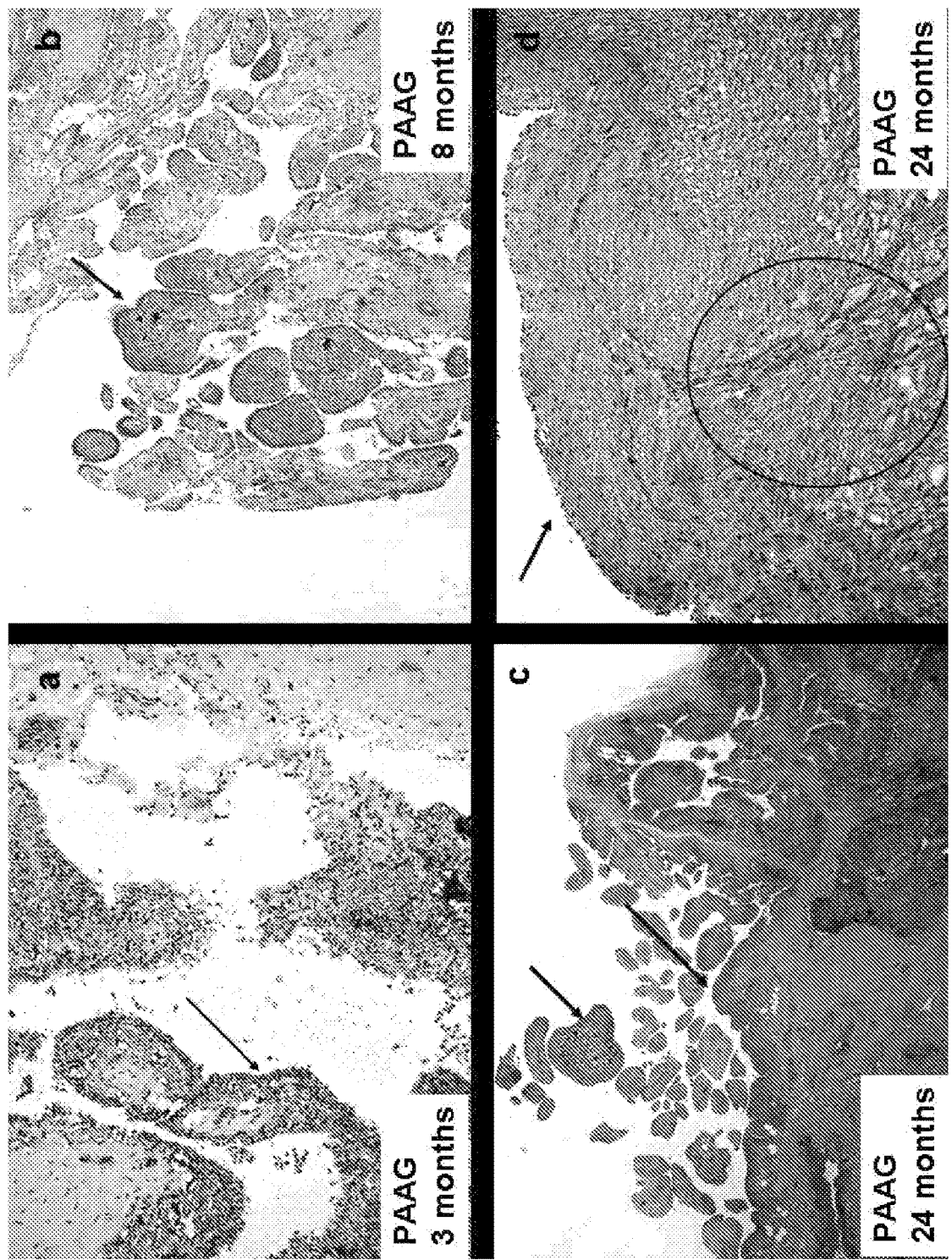
FIG. 2 shows a horse fetlock joint treated with PAAG for OA after 3 and 8 months (a, b) and after 24 months (c, d). The synovial surface lining is marked with arrows. The fine fibrous network inside the PAAG at 24 months is circled in d. HE×200 (a), HE×100 (b), HE×60 (c), and van Gieson/Alcian blue×150 (d).

Light microscopy findings: In the short term, 1 and 2 weeks post treatment, the PAAG appeared as an inner layer within the synovial lining intermixed with proliferating synovial cells, similar to the histology seen in the rabbit model. At 1 month the synovial cells had apparently relocated towards the surface, and at 3 months a distinct layer of synovial cells had formed on top of the integrated PAAG (FIG. 2a). The same pattern was found at 8 months (FIG. 2b) and at 24 months (FIGS. 2c and 2d). In general, there was no reduction in membrane thickness of the integrated PAAG, and at higher magnification, it could be seen that the PAAG had materialized itself as a thick integrated zone with at first scattered inflammatory cells, possibly synovial cells (FIG. 2a), and later with a fine fibrous network and very few inflammatory cells (FIG. 2d).

Summary of Results

Integration of the injected PAAG was evident at day 10 in the rabbit and by day 14 in the horse, with proliferation and invasion of synovial cells into the PAAG. By day 90 in rabbit joints and day 30 in horse joints, the PAAG had formed a sub-synovial layer, which was traversed by thin strands of connective tissue with vessels and covered by a novel synovial lining facing the joint cavity. This histological appearance persisted up to 2 years post-injection in horse joints.

Conclusion

Intra-articular injection of PAAG results in a stable, long-lasting sub-synovial layer of PAAG traversed with thin strands of connective tissue. Further, the injected PAAG did not contain macrophages and giant cells. Giant cells can arise in response to an infection and their presence in this context could accordingly have been a sign of inflammation or a non-stable integration of the PAAG. Thus, the current study surprisingly and uniquely demonstrated the formation of an analgesic, non-toxic, long-lasting and stable novel synovial lining layer after integration of the PAAG, which did not contain giant cells at any time (FIG. 1 (a, c, d) and FIG. 2 (a-d)).

Without being bound by theory it has been found that it is changes to synovial cell composition or cytokine production that provides prevention and/or treatment of painful synovitis in a mammal. Hence, intraarticular PAAG is present in joint synovium and persists over a time course.

Example 3—Clinical Study of Human Pain Score in Osteoarthritis Joints

Summary of Clinical Study

Title of Trial:

Retrospective and prospective observational study of Aquamid Reconstruction@ in patients with osteoarthritis of the knee.

Trial Period:

Patients were treated between March 2010 and January 2015 and followed up for at least 12 weeks after treatment.

Objectives:

The primary objective was to evaluate the outcome from baseline in WOMAC pain sub-scores at minimum 12 weeks after treatment with Aquamid Reconstruction®.

The secondary objectives were 1) To evaluate the outcome from baseline in total WOMAC score and the sub-scores for stiffness and functionality; 2) To assess patient's subjective perception of the treatment effectiveness at minimum 12 weeks after injection of Aquamid Reconstruction®.

Methodology:

This was a non-interventional follow up study of patients that had been treated off label with Aquamid Reconstruction for knee osteoarthritis.

The study consisted of a retrospective part where demographic and baseline characteristics were retrieved from patients medical records and a prospective, follow up part where patients with a baseline WOMAC pain sub-score could participate in the study. For the prospective part the majority of the data was collected from Case Report Forms. Patients were followed up after a minimum of 12 weeks after treatment with Aquamid Reconstruction®.

Number of Patients:

24 patients were included with a total of 32 knee joints treated.

Diagnosis and Criteria for Inclusion:

To be eligible for this study, patients must:

1) Have been treated with Aquamid Reconstruction@ for knee osteoarthritis, with subjective symptoms such as pain, swelling, excess fluid and limitation in joint movements and classified to have moderate to severe osteoarthritis according criteria set by the American College of Rheumatology and who previously have failed other treatments.

2) Have signed an informed consent form.

Criteria for Evaluation:

Efficacy:

The primary effectiveness endpoint is the change in the WOMAC pain sub-score from baseline to at least 12 weeks follow-up.

The secondary effectiveness endpoints are the change in the total WOMAC score, and stiffness and functionality sub-scores from baseline to at least 12 weeks as well as patient subjective perception of treatment effectiveness.

Results:

Efficacy:

There was a statistically significant improvement in mean change in the WOMAC pain sub-score (P=0.0002) and in each of the three secondary efficacy endpoints (total WOMAC score, and the stiffness and physical function sub-scores) from baseline to the last follow-up visit, (P=0.0012), (P=0.0008) and (P=0.0048), respectively.

Safety:

There were no serious adverse events reported. Mild and transient adverse effects generic to injection, such as swelling and discomfort, were observed in a few patients peri- and post-operatively, but no major complications such as infections were noted. No patient reported any discomfort/adverse events at follow-up.

Conclusion:

Aquamid Reconstruction@ is an effective and safe treatment for patients with osteoarthritis of the knee joint with a sustained effect.

Details of Clinical Study

Aquamid Reconstruction@ (AR) is a polyacrylamide hydrogel (PAAG).

1. Background

Between March 2010 and January 2015 24 patients with OA of the knee based on criteria set by the American College of Rheumatology were injected with AR. A total of 32 knee joints received treatment with AR. Prior to the injection a diagnosis of OA was determined by X-ray and the severity of OA was graded according to Kellgren and Lawrence which consists of 5 scores (0, None; 1, Doubtful; 2, Minimal; 3, Moderate; 4, Severe).

Effectiveness endpoints are change in the WOMAC sub-scores and total score and patient's subjective perception of treatment outcome at least 12 weeks after initial treatment.

The treatment with Aquamid Reconstruction@ in patients with OA in the knee joints was done in an off-label setting in patients who had not had an adequate response to other treatments (non-pharmacological and pharmacological) and who expressed a desire for a treatment where they could postpone or potentially totally avoid a total knee replacement.

1.1 Investigational Device

AR contains 2.5% polyacrylamide and 97.5% non-pyrogenic water. AR is biocompatible, non-biodegradable, stable and sterile.

The gel is provided in a sterile, pre-filled 1 ml sealed syringe. The gel was injected intra-articularly with a sterile 21G×2 inch (0.8×50 mm) needle.

Gel should be stored in dry environment in normal room temperature (under 30° C.).

It is intended for single use only. Before injection, it should be checked that the package is undamaged and has no visual alterations.

1.2 Method of Administration

The following approach was used for all patients injected with AR:

The procedure was done under aseptic conditions. Prior to injection the injection site was swapped in a radius of at least 5 cm around the injection site with chlorhexidine with alcohol three times with one minute interval. The injection was given in the joint space. If joint effusion was present, this was removed prior to injection, using the same needle. A 21 G×2" (0.8×50 mm) needle was used. The injection of the hydrogel was performed under local anesthesia (both inside the joint and directly at the injection site).

Injections were performed with the help of ultrasound in the lateral proximal recess. The patients were either lying down or sitting with the knee bent between 80°-90°.

The syringe, the needle and any unused material was discarded after the treatment session.

1.3 Dosing

Initially 1-5 ml were injected. If sufficient effectiveness was not obtained another 1-6 ml were injected after a minimum of two weeks. Some patients received up to 3 injections. See Table 6.

1.4 Trial Design

This non-interventional study consisted of a retrospective part where historical data were retrieved from the patients' medical records and a follow-up part where data was collected prospectively at follow up visits. The AR injections and the associated data were collected as part of the routine clinic work, which is why no specific follow-up intervals were planned nor was a strict assessment schedule followed.

Patients who had a baseline WOMAC score and followed-up for at least 12 weeks after the initial AR injection were included. The following data, recorded pre and/or post treatment, were obtained from the patients' medical records and CFRs:

Date(s) of treatment

Demographic characteristics (age, gender, height, weight)

Severity of knee osteoarthritis (Kellgren Lawrence grading)

Other treatments/interventions prior to AR treatment

Details about the treatment (volume injected)

WOMAC scores

Subjective perception of treatment outcome

Complications/adverse events

The patients either came to the clinic or were contacted over the telephone in order to complete the WOMAC questionnaire and provide their subjective perception of the effectiveness of treatment, as well as provide information about any complications/medical problems they might have had after treatment with AR.

1.5 Eligibility Criteria

In order to receive treatment with AR the patient had to fulfil the following criteria:
1. OA of the knee based on criteria set by the American College of Rheumatology
2. Signed informed consent form
2. Efficacy 2.1 Western Ontario and McMaster Universities (WOMAC) Osteoarthritis Index The Western Ontario and McMaster Universities (WOMAC) Osteoarthritis Index is a disease specific questionnaire designed to be completed by patients with hip and/or knee osteoarthritis in order to assess pain, stiffness, and physical function. The WOMAC questionnaire is available in a 5-point Likert-type and a 100 mm Visual Analogue Scale (VAS) format. VAS and Likert scale responses are highly correlated, however, the Likert scale is considered to be easier to administer as patients understand the check boxes associated with a word or a phrase better than marking an X on a continuous line. The Likert Scale version, which was used for all patients, uses the following descriptors for all items: none, mild, moderate, severe, and extreme. These correspond to an ordinal scale of 0-4.

The scores are summed for items in each subscale, with possible ranges as follows: pain=0-20, stiffness=0-8, physical function=0-68. A total WOMAC score is created by summing the items for all three subscales. Higher WOMAC scores indicate worse pain, stiffness, and functional limitations. The highest total score possible is 96.

The WOMAC Osteoarthritis Index consists of 24 items divided into 3 subscales:
Pain (5 items): during walking, using stairs, in bed, sitting or lying, and standing
Stiffness (2 items): after first waking up and later in the day
Physical Function (17 items): stair use, rising from sitting, standing, bending, walking, getting in/out of a car, shopping, putting on/taking off socks, rising from bed, lying in bed, getting in/out of bath, sitting, getting on/off toilet, heavy household duties, light household duties.

The questionnaire, which can be completed in person, over the telephone, or by computer, was primarily completed at the clinic when patients came for follow up visits, but some were completed over the phone.

2.2 Patient Subjective Perception

The patients were asked to indicate their perception of the treatment outcome by selecting one of the four alternatives to describe their condition: no pain (cured), improved, no change, worsened.

In addition, they were asked if they received a total knee replacement.

2.3 Safety

At each follow-up visit, the patients were asked about the occurrence of AEs/medical problems since the AR injection. Any complications or medical problems were recorded in the CRF. Peri-operative and post-operative complications/AEs, if any, were noted in the medical records.

3. Statistical Methodology 3.1 Sample Size Consideration

The number of patients was determined by the available data. Hence, neither sample size assessment nor power calculation was made.

3.2 General Approach for Reporting of Results

The collected data is summarized using descriptive statistics. Descriptive statistics for continuous parameters include as applicable number of observations (n), number of missing observations (nmiss), mean, standard deviation (SD), median, minimum (min) and maximum (max) values, while categorical parameters include frequency and percentage.

Estimates are presented with 95% confidence intervals where applicable. No correction for multiplicity will be applied. No formal hypothesis testing will be made.

3.3 Analysis and Reporting of Effectiveness Endpoint

The primary effectiveness endpoint is the change in WOMAC pain sub-score from baseline to the 12-weeks follow-up. The baseline value is defined as the last WOMAC pain sub-score assessed before or on the day of administration. The 12-weeks follow-up is defined as the first WOMAC pain sub-score assessed on or after 12-weeks (defined as relative day for assessment greater or equal to 12-weeks times 7 days, with day 1 being day of administration).

Descriptive statistics including mean and standard deviation for the primary endpoint will be presented. If applicable, a 95% confidence interval for the mean assuming normal distribution of the endpoint will be presented. The assumptions for use of normal distribution will be investigated graphically by presenting the distribution of the endpoint. If the assumptions are deemed not to be fulfilled, other approaches for analysis will be used, such as transforming the endpoint or using non-parametric methods. If applicable, the change will be corrected for baseline value.

For the purpose of exploratory analyses, further responder definitions may be introduced, such as defining response as at least 20% improvement from baseline.

3.4 Reporting of Safety Endpoint

The number of complications and adverse events will be summarized descriptively and presented as overall number and by timing (pre-administration and post-administration, and occurring at minimum 12 weeks after administration), and if applicable by injection sequence number.

TABLE 5

Demographic and Baseline Characteristics

| Characteristics | |
|---|---|
| Patients N (%) | 24 (100) |
| Gender (%) | |
| Male | 8 (33.3) |
| Female | 16 (66.7) |
| Age, years | |
| N | 24 |
| Mean ± SD | 66.0 ± 11.3 |
| Median | 68.0 |
| [Min, Max] | [36.0, 85.0] |
| Weight, kg | |
| N | 18 |
| Mean ± SD | 83.5 ± 16.8 |
| Median | 85.0 |
| [Min, Max] | [54.0, 135.0] |
| Height, m | |
| N | 18 |
| Mean ± SD | 1.7 ± 0.1 |
| Median | 1.7 |
| [Min, Max] | [1.6, 1.9] |

TABLE 5-continued

Demographic and Baseline Characteristics

| Characteristics | |
|---|---|
| BMI | |
| N | 18 |
| Mean ± SD | 28.3 ± 6.7 |
| Median | 26.6 |
| [Min, Max] | [17.8, 50.8] |
| Knees | |
| N | 32 |
| Left | 10 |
| Right | 6 |
| Both | 8 |
| OA score | N, knee (%) |
|  | 32 |
| 1 | 3 (9.4) |
| 2 | 7 (21.9) |
| 3 | 13 (40.6) |
| 4 | 9 (29.1) |
| Prior treatment | N (%) |
| ACP | 1 (3) |
| PRP | 3 (9) |
| Orthokine | 3 (9) |
| Cytostatic | 1 (3) |
| HA | 1 (3) |
| Anti-estrogen | 2 (6) |
| Housecleaning | 4 (12) |
| Menisc Removal | 1 (3) |
| Steadman Procedure | 1 (3) |
| Steroid | 12 (38) |

3.5 Treatment and Follow-up Information

Twenty-four patients with 32 knees received AR treatment. Of the 32 knees treated, 26 knees (81.3%) were re-injected; 23 knees received two injections and three knees received three injections.

The median total volume injected in each joint was 6.50 ml (range 2.0-11.0). For details, see Table 6. Most patients received the second injection between 2-14 weeks after the initial injection; however, three patients received the second treatment 26, 32 and 212 weeks after the first injection.

TABLE 6

Treatment Information Parameter

| | |
|---|---|
| Knees treated N (%) | 32 (100) |
| Number of AR injections N (%) | |
| 1 injection | 6 (18.8) |
| 2 injections | 23 (71.9) |
| 3 injections | 3 (9.4) |

TABLE 6-continued

Treatment Information Parameter

| Total volume injected (ml) | |
|---|---|
| Mean (SD) | 6.55 (2.83) |
| Median | 6.50 |
| [Min, Max] | [2.0, 11.0] |

Prior to treatment and at follow-up visits the patients completed the WOMAC questionnaire. At follow-up visits, the patients were also asked about their perception of the treatment outcome and if they have received a total knee replacement. The mean±SD (median) follow up time from first AR treatment was 428±522 (210) days (range 104-1744).

4. Efficacy Evaluation Data (Data not Shown, but Summarized Below).

4.1 Patient Subjective Perception of Treatment Outcome

The patient subjective assessment of the treatment outcome showed that 20 knees (62.6%) were classified as either "cured/no pain" (6.3%) or "improved" (56.3%). Eight knees (25.0%) were reported to have "no change" and 3 knees (9.4%) were "worsened". One patient had a total knee replacement of the left knee during the study ("removed").

The patient subjective perception of treatment outcome is provided in Table 7

TABLE 7

Patient subjective perception of treatment outcome

| Parameter | Knee N = 32 (100%) |
|---|---|
| No pain | 2 (6.3) |
| Improved | 18 (56.3) |
| No change | 8 (25.9) |
| Worsened | 3 (9.4) |
| Removed | 1 (3.1) |

The patients that reported they were pain-free (cured) or had improved also demonstrated the highest change in the WOMAC pain sub-score, (−10.0) and (−4.9), respectively. A similar relationship is seen for total WOMAC score and the two sub-scores (stiffness and physical function). For the WOMAC scores associated with the patient reported treatment outcome the results are shown in Table 8.

TABLE 8

WOMAC pain sub-score for patient reported treatment outcome

| Parameter | Knee N = 32 (%) | Change in WOMAC pain sub-score Mean (±SD) | Change in WOMAC total score Mean (±SD) | Change in WOMAC stiffness sub-score Mean (±SD) | Change in WOMAC function sub-score Mean (±SD) |
|---|---|---|---|---|---|
| No pain | 2 (6.3) | −10 (±1.4) | −45.5 (±2.1) | −3.0 (±0.0) | −32.5 (±0.7) |
| Improved | 18 (56.3) | −4.9 (±3.9) | −21.5 (±15.9) | −2.6 (±1.7) | −14.0 (±12.2) |
| No change | 8 (25.0) | 0.5 (±2.8) | 5.3 (±13.1) | −0.1 (±1.0) | 4.9 (±12.5) |
| Worsened | 3 (9.4%) | 1.0 (±2.6) | 12.0 (±13.9) | 2.3 (±2.9) | 8.7 (±8.4) |
| Removed1 | 1 (3.1%) | −7.0 | −32.0 | −1.0 | −24.0 |

5. Safety Evaluation 5.1. Adverse Events

There were no serious adverse events reported. Mild and transient adverse effects generic to injection, such as swelling and discomfort, were observed in a few patients peri- and post-operatively, but no major complications such as infections were noted.

No patient reported any discomfort/adverse events at follow-up.

The number of patients treated is limited which may account for the lack of complications observed. However, PAAG has demonstrated a good safety profile with few complications in other indications.

6. Conclusion

The WOMAC score reduction seen in this study of 32 knees followed for a median of 7 months after PAAG treatment was statistically significant for the total WOMAC score as well as all sub-scores. The placebo effect is known to last for up to 6 months for current non-invasive treatments. After that time, symptoms recur without re-injections.

The primary endpoint of the study—change in WOMAC pain sub-score—was reduced significantly (P=0.0002) by approximately 40% for all OA severity groups. OA severity group 1 & 2 demonstrated numerically larger effect on the pain score (median change −5.5) than OA severity group 3 & 4 (median change −2.0).

$_1$ Patient ID 54 received an injection in the left knee with an initial good response to treatment that decreased after two months where the patient came back and received a second injection in the left knee. At the same time point, the right knee was also injected with AR. Both the left and the right knee showed a good improvement and the patient was cycling 40 km a day. This improvement lasted for about 6 months and following a decrease of the effect in the left knee the patient was scheduled for a total knee replacement. A pre-treatment WOMAC for the right knee was not obtained, but this knee is doing excellent 42 months after injection. Post-treatment WOMAC was taken 3.5 months after AR injection.

Interestingly, the change in WOMAC pain sub-score was significant (P=0.0107) for OA severity score 3 and 4.

Surprisingly, the present inventors have found that polyacrylamide hydrogel (PAAG) is useful in the prevention and/or treatment of pain in humans suffering from osteoarthritis (OA).

Synovitis is present in many joints affected with osteoarthritis (OA). Hence, without being bound by a particular theory, the analgesic effect observed in this study on humans suffering from osteoarthritis is considered to be caused by the presence of a novel synovial lining layer and/or a novel sub-synovial layer after integration of the PAAG into the human joints and thus a reduction of synovial pain.

Example 4—Tissue Investigations of Knees of Human Patients

Background Clinic

The knee joints of two patient suffering from osteoarthritis were injected with PAAG (Aquamid), which by its passive integration and filler effect on the synovial membrane provided reduction or complete removal of pain. Depending on the severity of the osteoarthritis this pain relief lasted for up to 2 years and 5 months. After that TKA (total knee alloplasty, i.e. knee replacement) was performed.

Pathological Findings from TKAs

Bone, cartilage and soft tissue from standard TKA surgeries were obtained after removal of approximately the same amount of tissue in each surgery, corresponding to a tenth of the knee joint. Soft tissues and cartilage-covered bone were cut in small pieces and processed for histological examination. All tissue, with the exception of three quarters of the bone, was examined. The amount of soft tissue varied slightly from knee to knee.

Only a tenth of the knee joint tissue was removed during the TKA surgery, and an observed lack of integrated Aquamid is most likely a consequence of different Aquamid uptakes in different parts of the joint.

Patient 1

Clinic: A 77-year old woman with bilateral severe knee osteoarthritis was injected in both knees with 5 ml Aquamid on August 7 and Aug. 28, 2014 (total 10 ml per knee). The gel had helped for the first 2 out of the approximately 2½ years, but on Sep. 12, 2016, left side TKA was performed due to severe end-stage OA.

An abundance of fully integrated gel was seen within all the soft tissue examined. Areas of perivascular inflammation, streaks of connective tissue fibers and foci of clear cell macrophages were also seen within the synovial soft tissue. A deep-seated gel deposit containing giant cells gave the impression of a direct gel injection into the soft tissues and not, as expected, only into the cavity. There was at no point any gel in the cartilage or bone. The gel had been injected 2 years and 5 months previously.

Patient 2

Clinic: A 69-year old woman with moderate knee osteoarthritis was injected with a total of 3 ml Aquamid on 17 Mar. 2014. The Aquamid injection helped initially, but two years later the osteoarthritis pain had recurred and TKA was performed.

A well-integrated Aquamid gel was seen in one third of the biopsies. The gel was fully integrated with a mature network and scattered inflammatory and fibroblastic cells. There were no giant cells and no areas giving the impression of deep-seated gel injections directly into the soft tissues. There was at no point any gel in the cartilage or bone. The gel had been injected 2 years previously.

Conclusion

Aquamid gel becomes integrated into the synovial membrane by a combination of synovial lining transposition and ingrowth of surrounding host cells i.e. by formation of a sub-synovial layer and/or a novel synovial lining layer. The cellularity within the gel is lower than that within normal synovial tissue, and part of the pain-reducing effect of Aquamid injections is probably caused by the paucity of cells, blood vessels and associated nerves.

The invention claimed is:

1. A method of ameliorating synovitis in a mammal comprising:
   selecting a mammal to receive a sub-synovial layer or a novel synovial lining layer; and
   administering a polyacrylamide hydrogel to an intraarticular cavity of the mammal to generate the sub-synovial layer or novel synovial lining layer comprising said polyacrylamide hydrogel.

2. The method according to claim 1, wherein the sub-synovial layer or the novel synovial lining layer persists for up to 15 months.

3. The method according to claim 1, wherein the polyacrylamide hydrogel is administered by injection under sterile conditions.

4. The method according to claim 1, wherein the polyacrylamide hydrogel is administered by intraarticular injection.

5. The method according to claim 1, wherein 0.1-20 ml polyacrylamide hydrogel is administered by injection into the intraarticular cavity.

6. The method according to claim 1, wherein 0.1-20 ml polyacrylamide hydrogel is administered by injection into the intraarticular cavity at least twice.

7. The method according to claim 1, wherein 0.1-20 ml polyacrylamide hydrogel is administered by injection into the intraarticular cavity at regular intervals.

8. The method according to claim 1, wherein the mammal is a human, a racing animal or a companion animal.

9. The method of claim 1, wherein the mammal is a human and the polyacrylamide hydrogel is administered to a joint selected from the group consisting of a knee, a hip, an elbow, a metacarpal-phalangeal and interphalangeal joint in hands or feet, a sesamoid joint and the temporomandibular joint.

10. The method according to claim 1, wherein the mammal is a horse and the polyacrylamide hydrogel is administered to a fetlock, coffin, pastern, stifle, or knee joint of the hind leg.

11. The method according to claim 1, wherein the mammal is a dog and the polyacrylamide hydrogel is administered to the elbow of the front leg or the knee or hip joint of the hind leg.

12. The method of claim 1, wherein the mammal is suffering from arthritis, osteoarthritis, rheumatoid arthritis, lupus, or gout.

13. The method according to claim 12, wherein the mammal is suffering from osteoarthritis or rheumatoid arthritis.

14. A method of ameliorating synovitis in a mammal comprising:
    administering a polyacrylamide hydrogel to an intraarticular cavity of a mammal to generate a sub-synovial layer or a novel synovial lining layer comprising said polyacrylamide hydrogel; and
    evaluating said mammal for the formation of the sub-synovial layer or the novel synovial lining layer.

15. The method according to claim 14, wherein the sub-synovial layer or the novel synovial lining layer persists for up to 15 months.

16. The method according to claim 14, wherein the polyacrylamide hydrogel is administered by injection under sterile conditions.

17. The method according to claim 14, wherein the polyacrylamide hydrogel is administered by intraarticular injection.

18. The method according to claim 14, wherein 0.1-20 ml polyacrylamide hydrogel is administered by injection into the intraarticular cavity.

19. The method according to claim 14, wherein 0.1-20 ml polyacrylamide hydrogel is administered by injection into the intraarticular cavity at least twice.

20. The method according to claim 14, wherein 0.1-20 ml polyacrylamide hydrogel is administered by injection into the intraarticular cavity at regular intervals.

21. The method according to claim 14, wherein the mammal is a human, a racing animal or a companion animal.

22. The method of claim 14, wherein the mammal is a human and the polyacrylamide hydrogel is administered to a joint selected from the group consisting of a knee, a hip, an elbow, a metacarpal-phalangeal and interphalangeal joint in hands or feet, a sesamoid joint and the temporomandibular joint.

23. The method according to claim 14, wherein the mammal is a horse and the polyacrylamide hydrogel is administered to a fetlock, coffin, pastern, stifle, or knee joint of the hind leg.

24. The method according to claim 14, wherein the mammal is a dog and the polyacrylamide hydrogel is administered to the elbow of the front leg or the knee or hip joint of the hind leg.

25. The method of claim 14, wherein the mammal is suffering from arthritis, osteoarthritis, rheumatoid arthritis, lupus, or gout.

26. The method according to claim 25, wherein the mammal is suffering from osteoarthritis or rheumatoid arthritis.

* * * * *